(12) United States Patent
Kruidenier et al.

(10) Patent No.: US 8,691,747 B2
(45) Date of Patent: Apr. 8, 2014

(54) METHOD OF TREATMENT BASED ON ATAD2 INHIBITORS

(75) Inventors: Laurens Kruidenier, Stevenage (GB); Kevin Lee, Stevenage (GB); David Francis Tough, Stevenage (GB); David Matthew Wilson, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 13/879,635

(22) PCT Filed: Oct. 25, 2011

(86) PCT No.: PCT/EP2011/068675
§ 371 (c)(1),
(2), (4) Date: Apr. 16, 2013

(87) PCT Pub. No.: WO2012/055880
PCT Pub. Date: May 3, 2012

(65) Prior Publication Data
US 2013/0224204 A1    Aug. 29, 2013

(30) Foreign Application Priority Data
Oct. 27, 2010 (GB) .................................. 1018147.7

(51) Int. Cl.
*A61K 31/00* (2006.01)
(52) U.S. Cl.
USPC ............................................................ 514/1
(58) Field of Classification Search
None
See application file for complete search history.

(56) References Cited

FOREIGN PATENT DOCUMENTS

| WO | WO 2008/043561 | 4/2008 |
|----|----------------|--------|
| WO | WO 2008043561 A2 * | 4/2008 |
| WO | WO 2008/132176 | 11/2008 |
| WO | WO 2011/041264 | 5/2011 |

OTHER PUBLICATIONS

Ismahane, B., et al. "High-Resolution Comparative Genomic Hybridization of Inflammatory Breast Cancer and Identification of Candidate Genes." PLOS One, vol. 6(2), Feb. 9, 2011, pp. E16950/1-E16950/13.

* cited by examiner

*Primary Examiner* — Tracy Vivlemore
(74) *Attorney, Agent, or Firm* — Robert H. Brink (57) ABSTRACT

A method of treating autoimmune and inflammatory diseases or conditions in a mammal, such as a human, which comprises the administration of a inhibitor of the bromodomain-containing protein: ATAD2.

1 Claim, 5 Drawing Sheets

SEQUENCE LISTING

<160> NUMBER OF SEQ ID NOS: 9

<210> SEQ ID NO 1
<211> LENGTH: 21
<212> TYPE: DNA

```
<213> ORGANISM: Homo Sapiens

<400> SEQUENCE: 1
aaggcattta taaagatcga a                                              21

<210> SEQ ID NO 2
<211> LENGTH: 21
<212> TYPE: DNA
<213> ORGANISM: Homo Sapiens

<400> SEQUENCE: 2
ctggtactta ggcaccataa a                                              21

<210> SEQ ID NO 3
<211> LENGTH: 21
<212> TYPE: DNA
<213> ORGANISM: Homo Sapiens

<400> SEQUENCE: 3
ccggataaag aagaacggac a                                              21

<210> SEQ ID NO 4
<211> LENGTH: 21
<212> TYPE: DNA
<213> ORGANISM: Homo Sapiens

<400> SEQUENCE: 4
aagaataatt agcagcgtta a                                              21

<210> SEQ ID NO 5
<211> LENGTH: 20
<212> TYPE: DNA
<213> ORGANISM: Artificial Sequence
<220> FEATURE:
<223> OTHER INFORMATION: Sequence Primer

<400> SEQUENCE: 5
cggcaagacc atcactctgg                                                20

<210> SEQ ID NO 6
<211> LENGTH: 20
<212> TYPE: DNA
<213> ORGANISM: Artificial Sequence
<220> FEATURE:
<223> OTHER INFORMATION: Sequence Primer

<400> SEQUENCE: 6
aaagagtgcg gccatcttcc                                                20

<210> SEQ ID NO 7
<211> LENGTH: 27
<212> TYPE: DNA
<213> ORGANISM: Artificial Sequence
<220> FEATURE:
<223> OTHER INFORMATION: Sequence Primer
<221> NAME/KEY: modified_base
<222> LOCATION: 27
<223> OTHER INFORMATION: TAMRA

<400> SEQUENCE: 7
tggagcccag tgacaccatc gaaaatg                                        27

<210> SEQ ID NO 8
<211> LENGTH: 20
<212> TYPE: DNA
<213> ORGANISM: Artificial Sequence
```

-continued

```
<220> FEATURE:
<223> OTHER INFORMATION: Sequence Primer

<400> SEQUENCE: 8
tcaaatgccc tcctcccatc                                              20

<210> SEQ ID NO 9
<211> LENGTH: 20
<212> TYPE: DNA
<213> ORGANISM: Artificial Sequence
<220> FEATURE:
<223> OTHER INFORMATION: Sequence Primer

<400> SEQUENCE: 9
ttgtggtgca gccagaagtg                                              20
```

METHOD OF TREATMENT BASED ON ATAD2 INHIBITORS

CROSS-REFERENCE TO RELATED APPLICATIONS

This application is filed pursuant to 35 USC 371 as a United States National Phase Application of International Patent Application Serial No. PCT/EP2011/068675 filed on Oct. 25, 2011, which claims priority from 1018147.7 filed on Oct. 27, 2010 in the United Kingdom.

FIELD OF THE INVENTION

The present invention is concerned with new methods of treatment. More particularly, the present invention relates to methods for treatment or prevention of autoimmune and inflammatory diseases and conditions by inhibiting or modifying the expression or function of bromodomain-containing proteins. In a further aspect the invention relates to a method for identifying agents useful in said methods of treatment. The invention particularly describes the role of certain bromodomain-containing proteins, particularly ADAD2 in these diseases and conditions and their use as therapeutic and screening targets.

BACKGROUND OF THE INVENTION

Chromatin is the complex combination of DNA and protein that makes up chromosomes. It is found inside the nuclei of eukaryotic cells and is divided between heterochromatin (condensed) and euchromatin (extended) forms. A range of different states of condensation are possible and the tightness of this structure varies during the cell cycle, being the most compact during the process of cell division. The major components of chromatin are DNA and proteins. Histones are the chief protein components of chromatin, acting as spools around which DNA winds. The basic building blocks of chromatin are nucleosomes, each of which is composed of 146 base pairs of DNA wrapped around a histone octamer that consists of 2 copies of each H2A, H2B, H3 and H4. The functions of chromatin are to package DNA into a smaller volume to fit in the cell, to strengthen the DNA to allow mitosis and meiosis, and to serve as a mechanism to control expression and DNA replication. Chromatin contains genetic material serving as instructions to direct cell functions. The genomes of eukaryotic organisms are highly organised within the nucleus of the cell. The chromatin structure is controlled by a series of post translational modifications to histone proteins, notably histones H3 and H4, and most commonly within the "histone tails" which extend beyond the core nuclerosome structure. Histone tails tend to be free for protein—protein interaction and are also the portion of the histone most prone to post-translational modification. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Of all classes of proteins, histones are amongst the most susceptible to post-translational modification. Histone modifications are dynamic, as they can be added or removed in response to specific stimuli, and these modifications direct both structural changes to chromatin and alterations in gene transcription. Lysine acetylation is a histone modification that forms an epigenetic mark on chromatin for bromodomain-containing proteins to dock and in turn, regulate gene expression. Distinct classes of enzymes, namely histone acetyltransferases (HATs) and histone deacetylases (HDACs), acetylate or de-acetylate specific histone lysine residues (1).

The bromodomain is currently the only protein domain known to specifically bind to acetylated lysine residues in histone tails. Bromodomains, which are approximately 110 amino acids long, are found in a large number of chromatin-associated proteins and have now been identified in approximately 70 human proteins, often adjacent to other protein motifs (2,3). Proteins that contain a bromodomain may contain additional bromodomains, as well as other functional motifs. For example, many HATs also contain a bromodomain (2). Interactions between bromodomains and modified histones may be an important mechanism underlying chromatin structural changes and gene regulation. Bromodomain containing proteins have been implicated in disease processes including cancer, inflammation and viral replication. The development of inhibitors to bromodomains is thus an attractive means for controlling gene expression, and there is a need in the art to regulate bromodomain binding to acetylated lysine in order to control gene expression.

The present inventors have identified bromodomains involved in the inflammatory response. Inhibiting these bromodomains by inhibiting expression and/or function therefore would provide a novel approach to the treatment of autoimmune and inflammatory diseases or conditions.

SUMMARY OF THE INVENTION

Thus in one aspect there is provided a method of treating autoimmune and inflammatory diseases and conditions which comprises inhibiting one or more bromodomain-containing proteins in a mammal.

In a further aspect there is provided a method of treatment of autoimmune and inflammatory diseases and conditions in a mammal comprising administering a therapeutically effective amount of an inhibitor of bromodomain-containing protein ATAD2.

In a further aspect there is provided the use of a bromodomain-containing protein inhibitor in the manufacture of a medicament for the treatment of autoimmune and inflammatory diseases and conditions in a mammal.

In a further aspect the present invention provides the use of an inhibitor of the bromodomain-containing protein ATAD2, in the manufacture of a medicament for the treatment of autoimmune and inflammatory diseases and conditions.

In a further aspect the present invention provides an inhibitor of the bromodomain-containing protein ATAD2 for use in the treatment of autoimmune and inflammatory diseases and conditions In a further aspect there is provided a pharmaceutical formulation for use in the treatment of autoimmune and inflammatory diseases or conditions, comprising an inhibitor of the bromodomain-containing protein ATAD2, together with at least one pharmaceutical carrier.

In a further aspect, there is provided a method of screening for an inhibitor of the bromodomain-containing protein ATAD2, in particular comprising the step of determining whether the compound inhibits or the step of determining whether the compound activates the bromodomain-containing protein ATAD2.

DESCRIPTION OF DRAWINGS

FIG. 2. ATAD2 protein expression is increased after T cell activation. (A) Monocyte-depleted peripheral blood mononuclear cells were either left untreated (−) or treated with a T cell activating stimulus, anti-CD3+anti-CD28 (+) for 24 hours. ATAD2 protein expression was measured in total cell lysates by Western blotting. Data are shown for two independent donors. (B) Purified CD4$^+$ T-cells were plated out in 6 well plates at $3 \times 10^6$ cells per well in 4 mls of medium and 10 ng/ml of IL-2. The cells were then treated with PMA (10 ng/ml) and ionomycin 500 ng/ml; PHA-P 2.5 µg/ml; free anti-CD3 2 µg/ml and anti-CD3 (2 µg/ml) plus anti-CD28 (2 µg/ml) for 72 hours, or left untreated. ATAD2 expression was then detected by Western blot and expression of histone H3 used as a loading control.

DETAILED DESCRIPTION OF THE INVENTION

Various bromodomain-containing proteins have been identified and characterised. The following is particularly mentioned:
ATAD2:
The nucleic acid sequence of human ATAD2 mRNA is provided by the accession number NM_014109.3.
The amino acid sequence of human ATAD2 protein is provided by the accession number NP_054828.2.
As used herein the term "polypeptide" refers to an amino acid chain including a full-length protein, oligopeptides, short peptides and fragments thereof, wherein the amino acid residues are linked by covalent bonds.
As used herein a "variant" is a polypeptide comprising a sequence, which differs (by deletion of an amino acid, insertion of an amino acid, and/or substitution of an amino acid for a different amino acid) in one or more amino acid positions from that of a parent polypeptide sequence. The variant sequence may be a non-naturally occurring sequence, i.e. a sequence not found in nature.
As used herein the term "synthetic peptide" refers to a peptide, including a short peptide that has been synthesized in vitro. The term further encompasses peptides or short peptides that have been modified by substitution with unusual or non-natural amino acids.
As used herein "naturally occurring" as applied to an object refers to the fact that the object can be found in nature as distinct from being artificially produced by man.
As used here in a "fragment" or "subsequence" refers to any portion of a given sequence. It is to be understood that a fragment or subsequence of a sequence will be shorter than the sequence itself by at least one amino acid or one nucleic acid residue. Thus, a fragment or subsequence refers to a sequence of amino acids or nucleic acids that comprises a part of a longer sequence of amino acids (e.g. polypeptide).
As used herein the term "sequence identity" indicates a quantitative measure of the degree of homology between two amino acid sequences or between two nucleic acid sequences of equal length. If the two sequences to be compared are not of equal length, they must be aligned to give the best possible fit, allowing the insertion of gaps or, alternatively, truncation at the ends of polypeptide sequences or nucleotide sequences.
As used herein the term "nucleic acid molecule" refers to an oligomer or polymer of ribonucleic acid (RNA) or deoxyribonucleic acid (DNA) or mimetics thereof. This term includes molecules composed of naturally-occurring nucleobases, sugars and covalent internucleoside (backside) linkages which function similarly or combinations thereof.
As used herein a "polynucleotide sequence" (e.g. a nucleic acid, polynucleotide, oligonucleotide, etc.) is a polymer of nucleotides comprising nucleotides A, C, T, U, G, or other naturally occurring nucleotides or artificial nucleotide analogues, or a character string representing a nucleic acid, depending on context. Either the given nucleic acid or the complementary nucleic acid can be determined from any specified polynucleotide sequence.
As used herein, the term "inhibitor" can be any compound or treatment capable of inhibiting the expression and/or function of the bromodomain-containing protein, i.e. any compound or treatment that inhibits transcription of the gene, RNA maturation, RNA translation, post-translational modification of the protein, binding of the protein to an acetylated lysine target and the like. Thus "inhibiting the bromodomain-containing protein ATAD2" includes inhibiting the expression and/or function of the bromodomain-protein ATAD2.
The inhibitor may be of varied nature and origin including natural origin [e.g. plant, animal, eukaryatic, bacterial, viral] or synthetic [particularly an organic, inorganic, synthetic or semi-synthetic molecule]. For example it can be a nucleic acid, a polypeptide, a protein, a peptide or a chemical compound. In one aspect the inhibitor is selective for a particular bromodomain-containing protein with no activity against other bromodomain-containing proteins.
In one aspect the inhibitor is an antisense nucleic acid capable of inhibiting transcription of the bromodomain-containing proteins or translation of the corresponding messenger RNA. The antisense nucleic acid can comprise all or part of the sequence of the bromodomain-containing protein, or of a sequence that is complementary thereto. The antisense sequence can be a DNA, and RNA (e.g. siRNA), a ribozyme, etc. It may be single-stranded or double stranded. It can also be a RNA encoded by an antisense gene. When an antisense nucleic acid comprising part of the sequence of the gene or messenger RNA under consideration is being used, it is preferred to use a part comprising at least 10 consecutive bases from the sequence, more preferably at least 15, in order to ensure specific hybridisation. In the case of an antisense oligonucleotide, it typically comprises less than 100 bases, for example in the order of 10 to 50 bases. This oligonucleotide can be modified to improve its stability, its nuclease resistance, its cell penetration, etc. Perfect complementarily between the sequence of the antisense molecule and that of the target gene or messenger RNA is not required, but is generally preferred.

According to another embodiment, the inhibitor compound is a polypeptide. It may be, for example a peptide comprising a region of the bromodomain-containing protein, and capable of antagonising its activity. A peptide advantageously comprises from 5 to 50 consecutive amino acids of the primary sequence of the bromodomain-containing protein under consideration, typically from 7 to 40. The polypeptide can also be an antibody against the bromodomain-containing protein, or a fragment or derivative of such an antibody, for example a Fab fragment, a CDR region, or, more preferably, a single chain antibody (e.g. ScFv). Single chain antibodies are particularly advantageous insofar as they can act in a specific and intracellular fashion to modulate the activity of a target protein. Such antibodies, fragments, or derivatives can be produced by conventional techniques comprising immunising an animal and recovering the serum (polyclonal) or spleen cells (in order to produce hybridomas by fusion with appropriate cell lines).

Methods for producing polyclonal antibodies in various species are described in the prior art. Typically, the antigen is combined with an adjuvant (e.g. Freund's adjuvant) and administered to an animal, typically by subcutaneous injection. Repeated injections can be performed. Blood samples are collected and the immunoglobulin or serum is separated. Conventional methods for producing monoclonal antibodies comprise immunising of an animal with an antigen, followed by recovery of spleen cells, which are then fused with immortalised cells, such as myeloma cells. The resulting hybridomas produce monoclonal antibodies and can be selected by limiting dilution in order to isolate individual clones. Fab or F(ab')2 fragments can be produced by protease digestion, according to conventional techniques.

According to another embodiment, the inhibitor is a chemical compound, of natural or synthetic origin, particularly an organic or inorganic molecule, capable of modulating the expression or the activity of the bromodomain-containing protein. In a particular embodiment, the inhibitor is a small molecule.

As used herein, the "effective amount" means that amount of a drug or pharmaceutical agent that will elicit the biological or medical response of a tissue, system, animal or human that is being sought, for instance, by a researcher or clinician. Furthermore, the term "therapeutic amount" means any amount which as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. "Therapy" and "treatment" may include treatment and/or prophylaxis.

While it is possible that, for use in therapy, the inhibitor may be administered as the raw chemical, it is possible to present the active ingredient as a pharmaceutical composition. Accordingly, the invention further provides pharmaceutical compositions comprising an agent which inhibits one or more bromodomain-containing proteins, particularly ATAD2, and one or more pharmaceutically acceptable carriers, diluents, or excipients. The carrier(s), diluents(s) or excipient(s) must be acceptable in the sense of being compatible with the other ingredients of the composition and not deleterious to the recipient thereof. In accordance with another aspect of the invention there is also provided a process for the preparation of a pharmaceutical composition including the agent, or pharmaceutically acceptable salts thereof, with one or more pharmaceutically acceptable carriers, diluents or excipients. The pharmaceutical composition can be for use in the treatment and/or prophylaxis of any of the conditions described herein.

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by reducing the compound to a suitable fine size and mixing with a similarly prepared pharmaceutical carrier such as an edible carbohydrate, as, for example, starch or mannitol. Flavouring, preservative, dispersing and colouring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and colouring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The composition can also be prepared to prolong or sustain the release as for example by coating or embedding particulate material in polymers, wax or the like.

The compounds of the invention may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Dosage forms for nasal or inhaled administration may conveniently be formulated as aerosols, solutions, suspensions drops, gels or dry powders.

For compositions suitable and/or adapted for inhaled administration, it is preferred that the agent is in a particle-size-reduced form, and more preferably the size-reduced form is obtained or obtainable by micronisation. The preferable particle size of the size-reduced (e.g. micronised) compound or salt or solvate is defined by a D50 value of about 0.5 to about 10 microns (for example as measured using laser diffraction). Compositions adapted for administration by inhalation include the particle dusts or mists. Suitable compositions wherein the carrier is a liquid for administration as a nasal spray or drops include aqueous or oil solutions/suspensions of the active ingredient which may be generated by means of various types of metered dose pressurised aerosols, nebulizers or insufflators.

Aerosol formulations, e.g. for inhaled administration, can comprise a solution or fine suspension of the agent in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the agent, (preferably in particle-size-reduced form, e.g. in micronised form), and optionally a performance modifier such as L-leucine or another amino acid, cellobiose octaacetate and/or metals salts of stearic acid such as magnesium or calcium stearate.

Aerosol formulations are preferably arranged so that each metered dose or "puff" of aerosol contains a particular amount of a compound of the invention. Administration may be once daily or several times daily, for example 2, 3 4 or 8 times, giving for example 1, 2 or 3 doses each time. The overall daily dose and the metered dose delivered by capsules and cartridges in an inhaler or insufflator will generally be double those with aerosol formulations.

Pharmaceutical compositions adapted for vaginal administration may be presented as pessaries, tampons, creams, gels, pastes, foams or spray formulations.

Pharmaceutical compositions adapted for parental administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavouring agents.

Antisense or RNA interference molecules may be administered to the mammal in need thereof. Alternatively, constructs including the same may be administered. Such molecules and constructs can be used to interfere with the expression of the protein of interest, e.g., bromodomain and as such, modify gene expression. Typically delivery is by means known in the art.

Antisense or RNA interference molecules can be delivered in vitro to cells or in vivo, e.g., to tumors of a mammal. Nodes of delivery can be used without limitations, including: intravenous, intramuscular, intraperitoneal, intra-arterial, local delivery during surgery, endoscopic, subcutaneous, and per os. Vectors can be selected for desirable properties for any particular application. Vectors can be viral or plasmid. Adenoviral vectors are useful in this regard. Tissue-specific, cell-type specific, or otherwise regulatable promoters can be used to control the transcription of the inhibitory polynucleotide molecules. Non-viral carriers such as liposomes or nanospheres can also be used.

A therapeutically effective amount of the agent will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or more usually in a number (such as two, three, four, five or six) of sub-doses per day such that the total daily dose is the same.

The agent may be employed alone or in combination with other therapeutic agents.

The agent for use in the present invention may be used in combination with or include one or more other therapeutic agents and may be administered either sequentially or simultaneously by any convenient route in separate or combined pharmaceutical compositions.

The agent and pharmaceutical compositions contain the invention may be used in combination with or include one or more other therapeutic agents, for example selected from NSAIDS, corticosteroids, COX-2 inhibitors, cytokine inhibitors, anti-TNF agents, inhibitors oncostatin M, anti-malarials, immunosuppressive and cytostatics Methods of Treatment and Diseases Provided herein are methods of treatment or prevention of autoimmune and inflammatory conditions and diseases that can be improved by inhibiting bromodomain-containing proteins and thereby, e.g., modulate the level of expression of acetylation activated and acetylation repressed target genes. A method may comprise administering to a subject, e.g. a subject in need thereof, a therapeutically effective amount of an agent described herein.

Thus in one aspect there is provided the use of a bromodomain inhibitor in the manufacture of a medicament for treating autoimmune and inflammatory diseases and conditions.

In a further aspect there is provided a method of treatment of autoimmune and inflammatory diseases and conditions in a mammal comprising administering a therapeutically effective amount of a bromodomain inhibitor.

In a further aspect the present invention provides an inhibitor of the bromodomain-containing protein ATAD2 for use in the treatment of autoimmune and inflammatory diseases and conditions In one aspect the bromodomain-containing protein is ATAD2.

In one aspect the inhibitor inhibits the bromodomain-containing protein ATAD2.

Based at least on the fact that increased histone acetylation has been found to be associated with inflammation, a method for treating inflammation in a subject may comprise administering to the subject a therapeutically effective amount of one or more agents that decrease acetylation or restore acetylation to its level in corresponding normal cells.

Inflammation represents a group of vascular, cellular and neurological responses to trauma. Inflammation can be characterised as the movement of inflammatory cells such as monocytes, neutrophils and granulocytes into the tissues. This is usually associated with reduced endothelial barrier function and oedema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterised by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (for example, in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self tissues.

The aim of anti-inflammatory therapy is therefore to reduce this inflammation, to inhibit autoimmunity when present and to allow for the physiological process or healing and tissue repair to progress.

The agents may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knew, ankle, and foot, and conditions affecting tissues connecting muscles to bones such as tendons. Examples of musculoskeletal inflammation which may be treated with compounds of the invention include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular inflammation refers to inflammation of any structure of the eye, including the eye lids. Examples of ocular inflammation which may be treated with the compounds of the invention include blepharitis, blepharochalasis, conjunctivitis, dacryoadenitis, keratitis, keratoconjunctivitis sicca (dry eye), scleritis, trichiasis, and uveitis.

Examples of inflammation of the nervous system which may be treated with the compounds of the invention include encephalitis, Guillain-Barre syndrome, meningitis, neuromyotonia, narcolepsy, multiple sclerosis, myelitis and schizophrenia.

Examples of inflammation of the vasculature or lymphatic system which may be treated with the compounds of the invention include arthrosclerosis, arthritis, phlebitis, vasculitis, and lymphangitis.

Examples of inflammatory conditions of the digestive system which may be treated with the compounds of the invention include cholangitis, cholecystitis, enteritis, enterocolitis, gastritis, gastroenteritis, inflammatory bowel disease (such as Crohn's disease and ulcerative colitis), ileitis, and proctitis.

Examples of inflammatory conditions of the reproductive system which may be treated with the compounds of the invention include cervicitis, chorioamnionitis, endometritis, epididymitis, omphalitis, oophoritis, orchitis, salpingitis, tubo-ovarian abscess, urethritis, vaginitis, vulvitis, and vulvodynia.

The agents may be used to treat autoimmune conditions having an inflammatory component. Such conditions include acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schönlein purpura, Kawasaki's disease, lupus erythematosus, microscopic colitis, microscopic polyarteritis, mixed connective tissue disease, multiple sclerosis, myasthenia gravis, opsocionus myoclonus syndrome, optic neuritis, ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, lyme disease, morphea, psoriasis, sarcoidosis, scleroderma, ulcerative colitis, and vitiligo.

The agents may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celliac disease).

Other inflammatory conditions which may be treated with the agents include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi; transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome, Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, astopic dermatitis, drug hypersensistivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autroimmine) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosis, psoriasis, chronic pulmonary disease, and inflammation accompanying infectious conditions (e.g., sepsis).

The methods of treatment and uses of the invention can be used in mammals, particularly in humans.

The present invention also provides a method for identifying agents which may be candidate compounds for the treatment of autoimmune and inflammatory diseases or conditions comprising determining whether a compound is capable of inhibiting the following bromodomain-containing protein ATAD2.

Screening Methods

The present invention proposes, for the first time that the bromodomain-containing ATAD2, is a potential therapeutic target for the treatment of autoimmune and inflammatory diseases and conditions and/or cancer. Thus, the present invention provides a new target for the identification, validation, selection and optimisation of active agents on the basis of their ability to modulate the expression or activity of the bromodomain-containing protein ATAD2. Such active agents include inhibitors as described above.

The present invention thus pertains to a method of identifying, screening, characterising or defining an agent which is capable of modulating the activity of the bromodomain-containing protein ATAD2. The methods can be used for screening for example large numbers of candidate compounds for clinical use in inflammatory and autoimmune diseases or cancer.

The assays (screening methods) may be performed in a cell-based system, an animal system or by a cell free system. Such techniques will be apparent to a person skilled in the art and may be based on a measure of interaction [e.g. binding, displacement or competition assays) or a measure of a function of activity, transcription and the like.

Thus, for example, the present invention provides a method of testing the ability of an agent to modulate the expression of the bromodomain-containing protein ATAD2, particularly to inhibit expression. In another example the present invention provides a method of testing the ability of an agent to bind to and optionally modulate the activity of the bromodomain-containing protein ATAD2, particularly to inhibit activity. In a further example the present invention provides a method for testing the ability of an agent to modulate the activity of the bromodomain-containing protein ATAD2, particularly to inhibit activity.

Provided herein are screening methods for identifying agents that inhibit bromodomain-containing proteins as being potentially useful in the treatment of prevention of autoimmune and inflammatory diseases and conditions and/or cancer. One method involves screening for an inhibitor of bromodomain-containing protein activity, including the steps of contacting a peptide, which may be modified by acetylation, with a bromodomain, particularly the bromodomain-containing protein ATAD2 or a fragment thereof in the presence and in the absence of a test substance, and identifying a test substance as an inhibitor or activator of bromodomain activity. Test agents (or substances) for screening as inhibitors of the bromodomain can be from any source known in the art. They can be natural products, purified or mixtures, synthetic compounds, members of compound libraries, etc. The test substances can be selected from those that have been identified previously to have biological or drug activity or from those that have not.

In a further aspect the method of screening for an inhibitor of bromodomain-containing protein includes a binding assay. Thus a compound which inhibits the binding of the bromodomain-containing protein ATAD2 to its substrate can be identified in competition or direct binding assays. Both direct and competition binding assay formats are similar to the formats used in immunoassays and receptor binding assays and will be generally known to a person skilled in the art.

In one aspect the bromodomain-containing protein is ATAD2.

Typically the methods use peptides of the ATAD2 protein. In particular the methods use a human protein. More particularly the protein has the amino acid sequence of human ATAD2 protein as described in accession number NP_001420.2. or a fragment thereof or a sequence having at least 75%, 80%, 85%, 90%, 91%, 92%, 93%, 94%, 95%, 96%, 97%, 98% or 99% homology to the amino acid sequence of human ATAD2 protein or a fragment thereof.

Preferably the fragments are at least 110 amino acids long and include the bromodomain.

The present invention further contemplates analogues of the amino acid sequences formed by conservative amino acid substitution. The principle behind conservative amino acid substitution is that certain amino acid pairs have compatible side chains such that, when one amino acid is substituted for the other, there will be only minimal changes in the tertiary structure of the peptide. Rules for conservative substitutions are explained in Bowie et al. Science 247(1990) 1306-1310. It is an object of the present invention to utilise polypeptides, fragments and variants that retain the ability of the protein to bind substrate. I Where required, each of the polypeptides, fragments and variants, where required, may be provided either in purified or un-purified form, for example as cellular extracts or by purification of the relevant component from such extracts. Alternatively, the polypeptides, fragments and variants can be recombinantly produced by recombinant expression techniques, and purified for use in the assay. Alternatively, the polypeptides, fragments and variants can be expressed recombinantly in a cell for use in cell based assays.

Typically, a polynucleotide encoding the relevant component is provided within an expression vector. Such expression vectors are routinely constructed in the art and may for example involve the use of plasmid DNA and appropriate initiators, promoters, enhancers and other elements, such as for example polyadenylation signals which may be necessary and which are positioned in the correct orientation in order to allow full protein expression. Suitable vectors would be very readily apparent to those of skill in the art, such as those described in more detail in the examples of the present application. Promoter sequences may be inducible or constitutive promoters depending on the selected assay format.

As natural substrates for bromodomains have been described to include acetylated histone peptides, preferred substrates could comprise peptides corresponding to these sequences and modifications. Conversely, other peptides with suitable affinity for ATAD2 could be utilised.

Thus for example the substrate may be a peptide, such a synthetic peptide comprising N-terminal residues of histone 3 or 4, at least 10, 20, 30, 40, 50 or full length. The substrate may be at least 70%, 75%, 80%, 85%, 90%, 91%, 92%, 93%, 94%, 95%, 96%, 97%, 98%, 99%, homologous thereto.

It may be also preferred to use a substrate selected from bulk histones, synthetic peptides and nucleosomes.

The following examples are set forth to illustrate the effectiveness of the approach described in the present invention and to further exemplify particular applications of general processes described above. Accordingly, the following Example section is in no way intended to limit the scope of the invention contemplated herein.

EXAMPLES

To investigate whether bromodomain-containing proteins might represent targets for treatment of autoimmunity and inflammatory diseases, we screened an siRNA library targeting 43 bromodomain-containing proteins (Table 1) for effects on human macrophage function. siRNAs bind specifically to an mRNA transcript that bears a complementary nucleotide sequence and subsequently reduces expression of the protein encoded by that specific mRNA. Since a number of disparate factors can influence the whether an siRNA can effectively reduce expression of its target gene, and advanced algorithms capable of accurately predicting efficacious siRNAs have not yet been developed, it has been recommended to use a minimum of three to four siRNAs against a given target when conducting a screen (4). We used at least four distinct siRNAs targeting each gene, including ATAD2 (Table 2) for our studies.

TABLE 1

| List of bromodomain-containing protein targets in library |
|---|
| ASH1L |
| ATAD2 |
| ATAD2 |
| ATAD2B |
| BAZ1A |
| BAZ1B |
| BAZ2A |
| BAZ2B |
| BRD1 |
| BRD2 |
| BRD3 |
| BRD4 |
| BRD7 |

TABLE 1-continued

List of bromodomain-containing protein targets in library

BRD8
BRD9
BRDT
BRPF1
BRPF3
BRWD1
BRWD3
CECR2
CREBBP
ATAD2
FALZ
KAT2A
KAT2B
MLL
MLL4
PBRM1
PHIP
PRKCBP1
SMARCA2
SMARCA4
SP100
SP110
SP140
TAF1
TAF1L
TRIM24
TRIM28
TRIM33
TRIM66
ZMYND11
ZMYND11

TABLE 2

List of ATAD2 siRNA target sequences

| | |
|---|---|
| SEQID: 1 | AAGGCATTTATAAAGATCGAA |
| SEQID: 2 | CTGGTACTTAGGCACCATAAA |
| SEQID: 3 | CCGGATAAAGAAGAACGGACA |
| SEQID: 4 | AAGAATAATTAGCAGCGTTAA |

We tested the effect of introducing these siRNAs into primary monocyte-derived human macrophages. Macrophages are thought to make major contributions to autoimmunity and inflammation through the production of pro-inflammatory cytokines. Conversely, these cells can also produce anti-inflammatory cytokines which counteract inflammatory processes. Hence, we assessed the effect of siRNAs targeting bromodomain-containing proteins on the production of both pro- and anti-inflammatory cytokines. TNF-α was measured as an example of a pro-inflammatory cytokine, given its central role in autoimmune and inflammatory diseases (5), while IL-10 was measured because of its crucial function in inhibiting inflammation (6).

Figure 1:
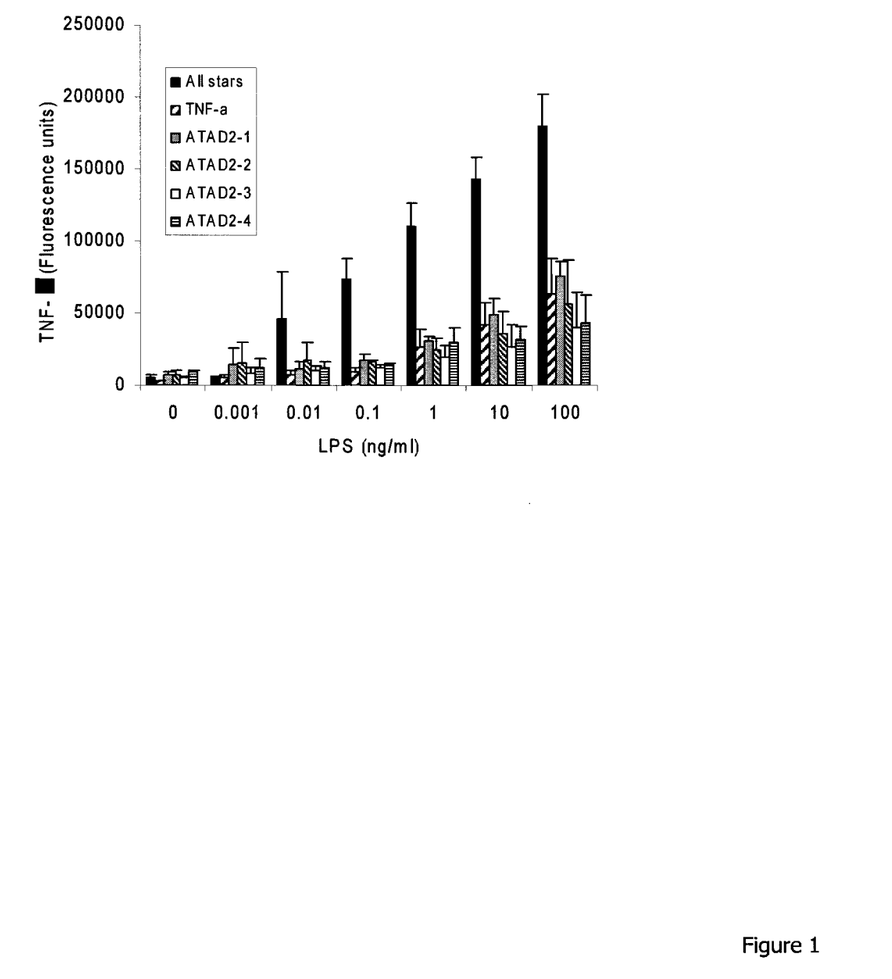
FIG. 1. siRNAs targeting ATAD2 inhibit TNF-α production by human macrophages. Monocyte-derived macrophages were transfected with: (1) 4 different siRNAs targeting ATAD2; (2) an siRNA targeting TNF-α as a positive control or; (3) A scrambled siRNA (All stars) as a negative control. The transfected macrophages were stimulated with the indicated concentrations of lipopolysaccharide (LPS), and the amount of TNF-α present in the medium 6 hours later was measured by MSD (results plotted as fluorescence units). The results show that all four siRNAs against ATAD2 inhibit TNF-α production to a similar level as the positive control (TNF-α siRNA). The data represent transfections done in triplicate for each siRNA and are the mean±SD for three different donors.

The siRNAs were introduced into macrophages by transfection, after which the cells were stimulated by treatment with lipopolysaccharide (LPS), a bacterial component. The quantities of TNF-α and IL-10 present in the medium six to eighteen hours after activation were measured. As shown in FIG. 1, siRNAs targeting ATAD2 were found to alter significantly cytokine production by macrophages. Specifically, siRNAs against ATAD2 inhibited LPS-induced production of the pro-inflammatory cytokine TNF-α. At all concentrations of LPS tested, 4 different siRNAs targeting ATAD2 inhibited the induction of TNF-α, and did so to a similar extent as did an siRNA which targeted TNF-α directly.

Figure 2:
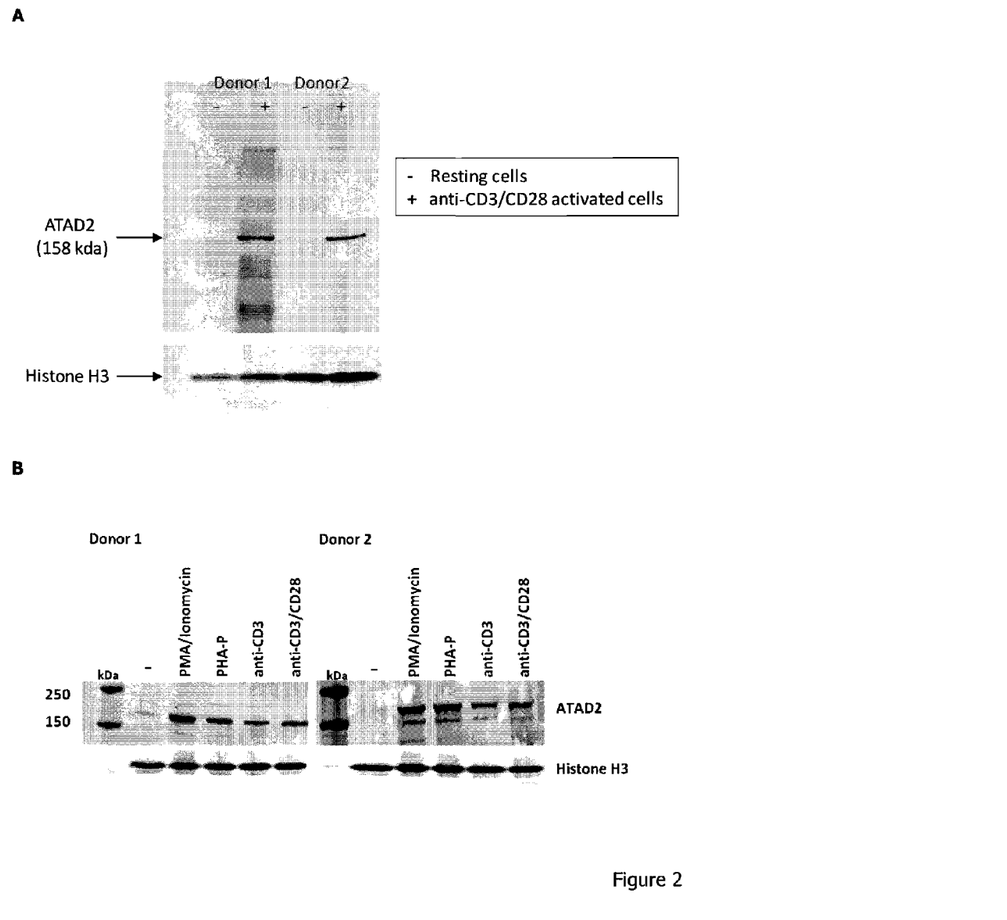

We also explored a possible role for ATAD2 in other immune cells. To investigate whether ATAD2 could contribute to the function of activated T cells, we compared ATAD2 protein expression before and after treating cells with a T cell activation stimulus. As shown in FIG. 2A, expression of ATAD2 protein increased upon treatment of monocyte depleted peripheral blood mononuclear cells (PBMCs) with anti-CD3 plus anti-CD28 antibodies, a stimulus that mimics T cell recognition of antigen and leads to T cell proliferation and cytokine production. Since monocyte-depleted PBMCs are highly enriched for T cells (both $CD4^+$ and $CD8^+$ T cells), the data suggested that T cells up-regulate expression of ATAD2 after activation. We further investigated this possibility using purified $CD4^+$ T cells. As shown in FIG. 2B, ATAD2 protein expression increased following treatment of $CD4^+$ T cells with anti-CD3 plus anti-CD28 antibodies. In addition, treatment of $CD4^+$ T cells with several other activation stimuli, including Phorbol Myristate Acetate (PMA)+ionomycin, phytohemagglutinin (PHA) and anti-CD3 antibodies alone, caused up-regulation of ATAD2 protein expression. The close link between T cell activation and increased expression of ATAD2 implies that ATAD2 may contribute to the T cell functional response.

Figure 3:
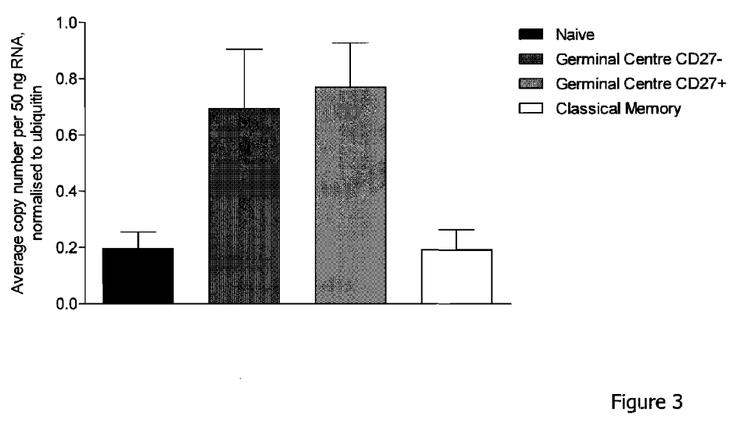
FIG. 3. Expression of ATAD2 mRNA in human tonsil B cell sub-sets. B cells isolated from human tonsils were separated using fluorescence activated cell sorting into naïve B cells (IgD+/CD38−/CD27−), germinal centre B cells (IgD−/CD38+/CD27− and IgD−/CD38+/CD27+) and classical memory B cells (IgD−/CD38−/CD27+). ATAD2 mRNA level were determined by quantitative RT-PCR. Data shown are the mean values from 7 donors (±SEM).
Figure 4:
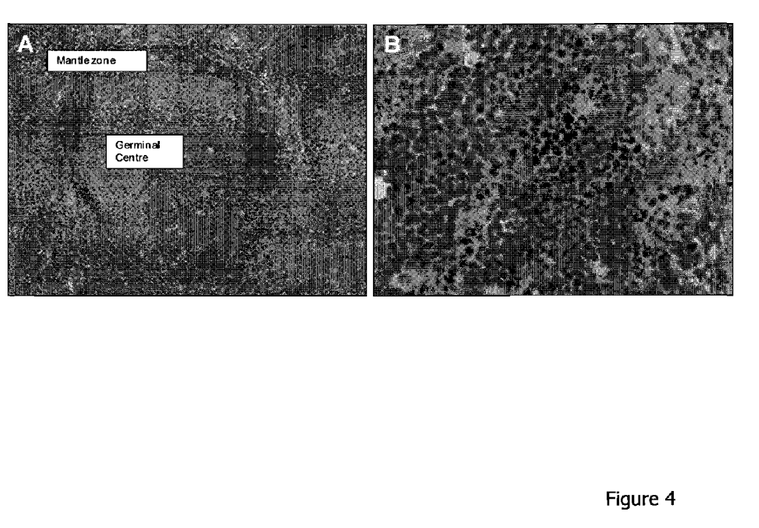
FIG. 4: Expression of ATAD2 in tonsillar tissue. ATAD2 expression in formalin fixed paraffin-embedded samples was detected using a polyclonal rabbit anti-ATAD2 and visualised with DAB chromagen (brown) at 10× magnification (A) and 40× magnification (B).

We also assessed ATAD2 expression in B cells in different activation states. Naïve, germinal centre, and memory B cell subsets were isolated from human tonsils and their mRNA levels of ATAD2 were measured by quantitative RT-PCR. ATAD2 mRNA expression was relatively low in the naïve B cell population but increased significantly in germinal centre B cells (FIG. 3). Classical memory B cells expressed low levels of ATAD2 similar to naïve B cells. These data indicate that ATAD2 expression is upregulated in B cells during the germinal centre reaction in vivo. Further evidence for this was provided by assessing ATAD2 protein expression in situ in human tonsillar tissue (FIG. 4). The correlation between high ATAD2 expression and activated germinal centre B cell status suggests that ATAD2 may have a function in T-dependent B cell responses to antigen, e.g. proliferation, differentiation, somatic hypermutation or class-switching.

Figure 5:
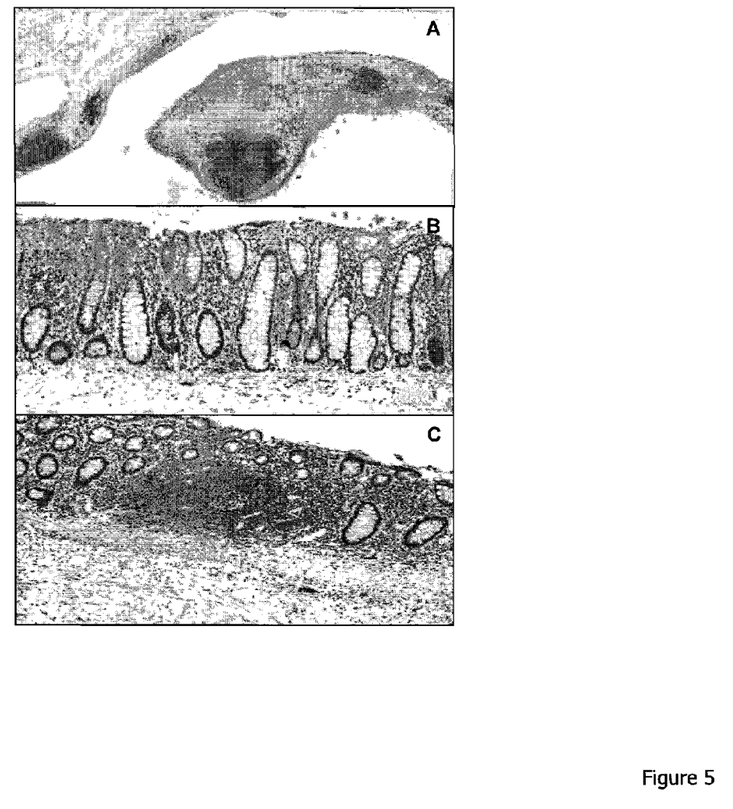
FIG. 5. Expression of ATAD2 in (A) Rheumatoid Arthritis, (B) Ulcerative Colitis and (C) Crohn's disease. ATAD2 expression in formalin fixed paraffin-embedded samples was detected using a polyclonal rabbit anti-ATAD2 and visualised with DAB chromagen (brown). Sections were counterstained with haematoxylin. N=4-6 donors per disease indication. Representative images are shown.

Finally, we assessed ATAD2 protein expression in various inflamed tissues from human inflammatory diseases (FIG. 5). Nuclear positivity for ATAD2 was evident in the mononuclear cell inflammatory infiltrates in rheumatoid arthritis (RA) synovial tissue (A) and also within the lamina propria of Ulcerative Colitis (B) and Crohn's diseased tissue (C). Where secondary follicular structures were formed, ATAD2 expression was present in mononuclear cells within the follicular centre but the surrounding mantel zone was mostly spared with few positive cells. No staining of polymorphonuclear cells was observed. Positive staining was also observed in the nerve plexi (nuclear and particular cytoplasmic), a proportion of the mucosal crypt epithelia cells (nuclear) of Ulcerative Colitis and Crohn's sections and endothelial cells of vessels in RA tissue. These results indicate that mononuclear cells in inflammatory infiltrates in a variety of autoimmune diseases express ATAD2.

Taken together, these results provide evidence for a previously unknown role for ATAD2 in inflammation. Thus, ATAD2 was shown to contribute to the generation of a pro-inflammatory macrophage cytokine profile; ATAD2 expression was shown increase upon T cell activation and B cell activation; and ATAD2 expressing were shown to be prominent in inflamed tissues from various human inflammatory autoimmune diseases. These findings indicate that approaches to inhibit the expression and/or function of this bromodomain-containing protein would be of benefit for the treatment of autoimmunity and inflammatory diseases and conditions.

Methods:

siRNA Studies in Macrophages

Cell Isolation:

Peripheral blood mononuclear cells (PBMCs) were prepared from 100 or 200 ml heparinized blood from healthy GSK volunteers by diluting samples 1:1 in PBS (w/o calcium and magnesium, Invitrogen), and layering them in 30 ml aliquots over 20 ml Ficoll-Paque Plus (Amersham Biosciences) in 50 ml Falcon tubes. Following centrifugation at 400×g, room temperature (RT) for 20 min with the brake off, the Buffy coat formed at the interface was transferred to fresh 50 ml tubes, diluted in PBS, centrifuged at 400×g (RT) for 10 min and the supernatant was removed. PBMCs were then resuspended in 3 ml 4° C. Miltenyi buffer with 0.5% BSA (Miltenyi Biotec), containing 300 µl MACS human CD14 MicroBeads (Miltenyi Biotec), and incubated at 4° C. for 15-25 min. Following this incubation, 4° C. Miltenyi buffer was added to a total volume of 50 ml, samples were spun down at 400×g (RT) for 10 min, supernatant was removed and cells were resuspended in 4 ml 4° C. Miltenyi buffer. Subsequently, 4 MACS LS Separation columns (Miltenyi Biotec) were placed in a magnetic holder and equilibrated with 3 ml Miltenyi buffer. The cell suspension was then divided onto these columns after which columns were washed with 3×3 ml 4° C. Miltenyi buffer. Bound CD14+ cells were subsequently eluted by removing columns from their magnetic holder, placing them over a 15 ml Falcon tube, and plunging 5 ml Miltenyi buffer through the columns using a supplied syringe barrel (Miltenyi Biotec). Eluted cell suspensions were spun down at 400×g (RT) for 10 min, resuspended in 2 ml culture medium (RPMI 1640 medium (Invitrogen) supplemented with 2 mM L-glutamine (Invitrogen), 100 units/ml penicillin (Invitrogen) and 100 µg/ml streptomycin (Invitrogen)) with 5% foetal bovine serum (FBS, heat-inactivated, Invitrogen) and counted using a haemocytometer, following which culture medium was added to a final concentration of 200,000 cells/ml.

Cell Culture and Transfection:

CD14+ monocyte suspensions were incubated in culture medium containing 5% FBS and 100 ng/ml hrM-CSF (R&D Systems) at 37° C. in a humidified atmosphere with 5% CO2 for six days. After 6 days of differentiation, cells were transfected with siRNA as follows. siRNAs were prepared at 200 nM (10× final concentration), in Optimem media (Gibco, Invitrogen). Diluted siRNA was mixed with an equal volume of Gemini transfection reagent (7) (10 µg/ml in Optimem). Mixtures were left to complex for 20-30 mins before 4 times the volume of macrophage medium (5% FBS RPMI) was added. Most of the media was removed from the cells, and replaced with diluted complex. Plates were sealed with gas permeable sealers and incubated for 48 h. Cells were then stimulated with by adding various concentrations of LPS and incubated for 6-18 h. Supernatants were taken off and assayed for IL-10 and TNF-α or they were centrifuged, transferred to fresh plates, and stored at −80° C. until analysis. Cytokines were assayed using MSD plates and read in a MSD Sector 6000 plate reader.

Hit Calling in siRNA Screens

In some studies, the function of bromodomain-containing proteins was assessed as part of large screens including siRNAs targeting both bromodomain- and non-bromodomain-containing proteins. Using the response library data, a robust mean and standard deviation was calculated on a plate by plate basis for each donor for each reporter cytokine. Two cut offs were also calculated to find the extreme 10% of the data in each tail. Any response greater than the robust mean plus 1.3 time the robust standard deviation was deemed an increasing hit and any response less than the robust mean minus 1.3 times the robust standard deviation was deemed an inhibited hit. The analysis used log responses, using log to the base 10.

Assessment of ATAD2 Protein Expression in Monocyte-Depleted PBMCs

Peripheral blood mononuclear cells (PBMCs) were isolated from human heparinised blood using Accupsin tubes (Sigma) and Ficoll Paque (GE Healthcare) density centrifugation. CD14+ cells were depleted using anti-CD14 beads and LS columns (MACS, Miltenyi Biotech). The eluate contains non CD14+ cells, predominantly lymphocytes, including both T cells and B cells. T cells were activated by incubating the monocyte-depleted PBMCs for 24 hours at 37° C. with beads conjugated to anti-CD3 and anti-CD28 antibodies (Dynabeads, human T-activator CD3/CD28, Invitrogen).

Total cell lysates were prepared as follows. Cells were spun down for 5 minutes at 1,200 rpm and the pellet was washed with 5 mL PBS. The pellet was resuspended in 30 µL of water and transferred into an Eppendorf tube. 30 µL of the denaturing mix (275 µL of water; 375 µL of NuPAGE®LDS Sample Buffer (4×), Invitrogen; and 100 µL of DTT 1.5M) was added and the samples were frozen at −20° C. until use. SDS-PAGE Samples were heated for 5 min at 80° C. (thermobloc) and then sonicated for 5 seconds at 10 microns to break the DNA. Samples were spun and mixed by pipeting. 40 µL of samples and 5 µL of See Blue®Plus 2 Prestained standard (1×) (Invitrogen) were loaded on a NuPAGE®4-12% Bis-Tris Gel 1.5 mm×10 well (Invitrogen). The samples were run for an hour at 100 mA/gel in MOPS buffer 1× under reducing conditions.

Proteins were transferred to membranes by semi-dry transfer using the kit iBlot™Gel Transfer Stacks Nitrocellulose Mini (Invitrogen), program 2, 23 Volts for 6 minutes. For detection, the nitrocellulose membrane was incubated with 10 mL of PBS containing 3% non-fat milk, pH 7.4 (Sigma) for 2-3 hours at room temperature with shaking, to block non specific sites. The primary antibody (anti-ATAD2, HPA029424 Prestige antibody, Sigma used at 1:500 in blocking buffer) was added and the membrane was incubated overnight with shaking. The membrane was washed in mQ PBS-0.1% Tween 20 to eliminate excess primary antibody: 5 quick washes, one wash for 30 minutes, 5 quick washes, one wash for 30 minutes. The secondary antibody (anti-rabbit-HRP, Sigma, dilution=1:20,000) was added and the membrane was incubated for one hour at RT with shaking and washed in PBS-0.1% Tween 20 as described above. The image of the membrane was captured using the Supersignal® West Femto Maximum Sensitivity Substrate kit (Thermo Scientific) and the LAS-3000 chemiluminescence imager (Fujifilm). The antibodies were stripped off and the membrane was re-probed with an anti-histone H3 antibody (Abcam) used at 1:2,500. Histone H3 served as loading control.

Assessment of ATAD2 Protein Expression in CD4+ T Cells

Peripheral blood mononuclear cells were isolated from peripheral blood donated by a healthy donor by centrifugation (800 g) over Histoplaque™. CD4+ T-cells were then isolated by negative selection using magnetic bead separation and re-suspended in primary cell medium to $1 \times 10^6$ cell/ml (RPMI 1640+10% heat inactivated foetal bovine serum, 2 mM L-glutamine and 100 U/ML penicillin and 100 mgs/ml streptomycin. The cells were then stimulated as described in FIG. 2B and incubated at 37 5% CO2 for 72 hours. The cells were then harvested, centrifuged to a pellet (800 g), dissolved in 200 µl of SDS sample buffer, probe sonicated for 30 seconds and centrifuged (1000 g). Samples were then analysed by Western blot analysis with the samples run on 4%-12% bis-tris electrophoresis gels with MOPS running buffer and transferred onto nitrocellulose membranes in transfer buffer plus 20% methanol. Membranes were blocked with Odyssey blocking buffer for 1 hour and then probed with anti-ATAD2 (1:500) and anti-histone H3 (1:3000) diluted in odyssey buffer. The incubation was over night. After washing in TBST the membranes were probed with donkey anti-rabbit Alexa Fluor™ 680 (1:6000) diluted in TBST (1 hour) and then after further washes with TBST analysed on the Odyssey fluorescent scanner.

Assessment of ATAD2 mRNA Expression in Tonsil B Cells

B-lymphocytes were isolated from human tonsils using a negative selection human B cell purification kit (MACS B cell isolation kit II, Miltenyi Biotech, cat. no. 130-091-151), according to the manufacturer's instructions. The purified B cells were stained for IgD, CD27, and CD38, using fluorescently labelled antibodies described previously. B cell subpopulation were sorted using a BD FACS Aria with the gating for a) $IgD^+/CD38^-/CD27^-$, b) $IgD^-/CD38^+/CD27^-$, c) $IgD^-/CD38^+/CD27^+$, d) $IgD^-/CD38^-/CD27^-$. $1 \times 10^6$ cells were collected for each subset in ice cold FCS, washed once in PBS, and then lysed for mRNA extraction (Qiagen, RNeasy kit) and analysis by QRT-PCR. In brief, the concentrations of the mRNA samples were measured using a NanoDrop spectrophotometer and reverse transcription of the appropriate quantity of mRNA was performed using SuperScript III First-Strand Synthesis SuperMix for qRT-PCR (Invitrogen, Product No. 11752250) according to the manufacturer's instructions. Q-PCR was performed using an ABIPRISM 7900HT machine. The following gene-specific primer/probe sets were used: Ubiquitin forward primer SEQ ID: 5 (CGGCAAGAC-CATCACTCTGG), Ubiquitin reverse primer SEQ ID: 6 (AAAGAGTGCGGCCATCTTCC), Ubiquitin probe (6-FAM-SEQ ID: 7 TGGAGCCCAGTGACACCATC-GAAAATG-TAMRA), ATAD2 forward primer SEQ ID: 8 (TCAAATGCCCTCCTCCCATC), ATAD2 reverse primer SEQ ID: 9 (TTGTGGTGCAGCCAGAAGTG). SYBR Green Master Mix (Invitrogen, Product No. 4364346) was used with the ATAD2 primer set. Data analysis of the qRT-PCR was performed using the software SDS 2.3 (Applied Biosystems), and MS Office Excel 2007. The former program calculated mRNA concentrations based on a standard curve of diluted genomic DNA. In the latter program the sample mRNA copy numbers were calculated for each gene and normalised to the house-keeping gene ubiquitin, by dividing the copy number of the cytokine gene by average ubiquitin copy number for that sample.

Assessment of ATAD2 Protein Expression in Tissues

Formalin fixed paraffin-embedded (FFPE) samples were obtained from commercial tissue banks. Samples were ethically collected and fully consented to meet the conditions of the UK 2006 Human Tissue Act. Where samples were prospectively collected they were again collected under LREC guidance and patients fully consented. Samples were formalin fixed for 24 hours and processed to paraffin wax using standard protocols. For immunohistochemistry, sections were hydrated and then antigen retrieved using either a microwave protocol or using 'on-board' instrument retrieval. Sections were labelled on either a Leica BondMax or a Ventana Discovery instrument. ATAD2 expression was detected using an in house generated rabbit anti-ATAD2 polyclonal antibody. Sites of antibody binding were visualised using either proprietary polymer amplification (Leica) or an avidin biotin system (Ventana) with 3,3'-Diaminobenzidine (DAB) as a chromagen and counterstained with haematoxylin in both instances. Sections were scanned and analysed using a Hamamatsu Nanozoomer.

Materials:

Miltenyi Buffer: PBS w/o Ca and Mg, 0.5% BSA, 5 mM EDTA

Miltenyi (MACS) CD14 Beads: CD14 MicroBeads, human 2 ml, contains 0.1% BSA, 0.05% Azide.

BSA: Albumin, Bovine Fraction V Powder (Sigma A-1933)

EDTA: Ethylenediaminetetraacetic acid (Sigma E-7889). Stock conc-0.5M siRNAs: All siRNAs were obtained from Qiagen.

PHA-P; PMA; ionomycin; methanol and anti-ATAD2 (rabbit polycolonal) purchased from Sigma.

4%-12% bis-tris gels; nitrocellulose; MOPS running buffer; transfer buffer and donkey anti-rabbit Alexa Flour™ 680; RMPI 1640; foetal bovine serum; L-glutamine; penicillin; streptomycin and six well plates purchased from Invitrogen.

IL-2 purchased from R&D systems

CD4+ T-cell isolation kit purchased from Miltenyi biotech

Anti-histone H3 (rabbit polyclonal) purchased from Abcam

Anti-CD3 (clone UCHT1) and anti-CD28 (clone 28.2) purchased from BD pharmingen.

Lane markers purchased from Li-Cor.

REFERENCES (1) Struhl K. Histone acetylation and transcriptional regulatory mechanisms. Genes Dev. 1998 Mar. 1; 12(5):599-606.
(2) Jeanmougin F, Wurtz J M, Le Douarin B, Chambon P, Losson R. The bromodomain revisited. Trends Biochem Sci. 1997 May; 22(5):151-3.
(3) Tamkun J W, Deuring R, Scott M P, Kissinger M, Pattatucci A M, Kaufman T C, Kennison J A. Brahma: a regulator of Drosophila homeotic genes structurally related to the yeast transcriptional activator SNF2/SWI2. Cell. 1992 Feb. 7; 68(3):561-72.
(4) Wolters N M, MacKeigan J P. From sequence to function: using RNAi to elucidate mechanisms of human disease. Cell Death Differ. 2008 May; 15(5):809-19.
(5) Sethi G, Sung B, Kunnumakkara A B, Aggarwal B B. Targeting TNF for Treatment of Cancer and Autoimmunity. Adv Exp Med Biol. 2009; 647:37-51.
(6) Mosser, D M, Zhang, X. Interleukin-10: new perspectives on an old cytokine. Immunol Rev. 2008; 226: 205-218.
(7) Wettig, S D, Verrall, R E, Foldvari, M. Gemini surfactants: a new family of building blocks for non-viral gene delivery systems. Curr. Gene Ther. 2008 Feb. 8 (1):9-23.

The invention claimed is:

1. A method of treating autoimmune and inflammatory diseases and conditions in a human in need thereof, which comprises the administration of a therapeutically effective amount of an inhibitor of the bromodomain-containing protein ATAD2.

* * * * *